United States Patent [19]

Bauer et al.

[11] Patent Number: 5,714,103
[45] Date of Patent: Feb. 3, 1998

[54] PROCESS FOR THE PRODUCTION OF SHAPED ARTICLES HAVING A PREDETERMINED PORE STRUCTURE

[75] Inventors: Jörg Bauer; Andrea Bauer, both of Flomborn, Germany

[73] Assignee: Merck Patent Gesellschaft Mit Beschrankter Haftung, Darmstadt, Germany

[21] Appl. No.: 295,644

[22] PCT Filed: Feb. 12, 1993

[86] PCT No.: PCT/EP93/00344

§ 371 Date: Aug. 26, 1994

§ 102(e) Date: Aug. 26, 1994

[87] PCT Pub. No.: WO93/16865

PCT Pub. Date: Sep. 2, 1993

[30] Foreign Application Priority Data

Feb. 27, 1992 [DE] Germany ............. 42 05 969.0

[51] Int. Cl.$^6$ .............. A61F 2/28; B29C 67/02; B29C 35/02; B22F 7/02
[52] U.S. Cl. ............ 264/109; 264/113; 264/125; 623/901
[58] Field of Search ............ 264/109, 112, 264/113, 125; 623/901

[56] References Cited

U.S. PATENT DOCUMENTS

| | | | |
|---|---|---|---|
| 4,543,341 | 9/1985 | Barringer et al. | 264/56 |
| 4,698,192 | 10/1987 | Kuze et al. | 264/109 |
| 4,940,412 | 7/1990 | Blumenthal | 623/901 |
| 5,030,391 | 7/1991 | Sumita et al. | 264/5 |
| 5,204,055 | 4/1993 | Sachs et al. | 264/113 |
| 5,354,414 | 10/1994 | Feygin | 264/113 |
| 5,368,791 | 11/1994 | Uchida et al. | 264/113 |
| 5,370,692 | 12/1994 | Fink et al. | 623/901 |

FOREIGN PATENT DOCUMENTS

| | | |
|---|---|---|
| 253506 | 1/1988 | European Pat. Off. |
| 1-173691 | 7/1989 | Japan . |
| 2223928 | 1/1991 | United Kingdom . |

OTHER PUBLICATIONS

Technische Rundschau Bd. 83, Nr. 20, 17 May 1991.
Patent Abstracts of Japan, vol. 013445, 6 Oct. 1989.
The Encyclopedia Americana, International Edition, vol. 4, pp. 204–205, © 1978.

*Primary Examiner*—James Engel
*Assistant Examiner*—Kenneth M. Jones
*Attorney, Agent, or Firm*—Millen, White, Zelano, & Branigan, P.C.

[57] ABSTRACT

The invention relates to a process for the production of porous shaped articles having a predetermined pore structure by shaping a composition which can undergo plastic deformation and then be solidified, which is characterized in that the shaped article is built up in the form of layers by repeated sequence of the steps A. Production of a layer of the composition structured in an image-wise manner corresponding to the pore system, and B. Solidification of the layer the image structures of the individual layers being transferred from corresponding models. This process can preferably be used for the production of shaped articles having a three-dimensionally interconnecting pore system, and in particular for the production of shaped implants having the pore system of natural bone.

8 Claims, No Drawings

PROCESS FOR THE PRODUCTION OF SHAPED ARTICLES HAVING A PREDETERMINED PORE STRUCTURE

The invention relates to a process for the production of shaped articles having a predetermined pore structure. This process can preferably be used for the production of shaped articles having a three-dimensionally interconnecting pore system, and in particular for the production of shaped implants having the pore system of natural bones.

The production of shaped articles, regardless of from what substance and material, having a predetermined pore structure of course presents problems. This is the case above all if, instead of a material- and processing-related statistically uniform porosity or instead of a monodimensional pore alignment, a locally different structuring and/or a defined pore system in several dimensions is desired. Thus, known techniques for the production of porous materials or bodies, such as, for example, foaming of suitable materials or incorporation of soluble or gas-forming substances into corresponding matrix materials, lead to essentially statistically uniform pore structures. In extrusion operations on plastic or plasticizable materials, essentially monodimensionally aligned pore systems can at best be produced.

These generally applicable problems will now be illustrated in more detail by the example of shaped implants for bone replacement and the decisive requirements in this context.

Bone replacement materials for the production of shaped implants can be classified into the two main groups of bioinert and bioactive materials. Bioinert materials include physiologically acceptable metals, oxide ceramics and certain plastics. Bioactive materials, which cause a positive physiological effect of whatever type in the organism, include materials based on calcium minerals, biopolymers and composite materials based on the materials mentioned. Bioabsorbable materials form a subgroup of these.

Bioactive implant materials enjoy preferred interest, since they cause stimulation of bone growth and thereby improved healing of the implant into the bone and the endogenous tissue.

Shaped articles of ceramic material are primarily employed for replacement of load-bearing bone structures which must withstand high mechanical stresses. Examples of these are bone prostheses and bone connecting elements, such as, for example, medullary nails, bone screws and osteosynthesis plates.

Because it is related chemically to the mineral phase of natural bone, bone replacement materials based on calcium phosphate ceramics are regarded as bioactive. The mineral phase of natural bone comprises chiefly the calcium phosphate compound hydroxyapatite. Hydroxyapatite of synthetic or organic origin, for example from natural bone material, is therefore a raw material which is often used for production of implants for bone replacement.

Experience shows that the strength of the fusion of compact calcium phosphate ceramic with existing bone is mostly unsatisfactory. Porous calcium phosphate ceramics show more favorable growing-in properties.

The ceramic implant materials based on calcium phosphate which are currently available are divided into two basic groups.

The first group uses synthetically prepared calcium phosphates, which are shaped to compact or porous bodies and then sintered to give the ceramic. The advantage of these materials of course lies in the fact that the synthetic build-up allows selected chemical compositions to be obtained with a high accuracy and reproducibility without problems. The standardizability of the composition is essential for medical uses.

A decisive disadvantage of synthetic materials is that porous bodies can be produced only with great difficulty and with great effort. There has therefore been no lack of attempts to produce porous shaped articles from calcium phosphate ceramics by a procedure in which, for example, organic fibers, woven fabric or braided fabric or a body of spongy structure of organic material are embedded in a mineral matrix, and this is then baked thoroughly before or during sintering to give the ceramic. Such a process is described, for example, in EP 253 506. Because of the structural differences from natural bone, the involved production procedure and the only insignificantly improved properties in respect of healing in, such shaped implants have hitherto not yet become accepted. It is thus to date not yet possible to emulate the porosity characteristic of natural bone, in particular, for example, the open porosity of spongiosa bone, with shaped articles of synthetic materials. However, it has been found that precisely this porosity which is typical of bone is essential for rapid, firm and permanent bonding of the implant with the endogenous bone.

The second group is based on biological systems, such as bone, algae and coral, which are mineralized by various treatments and converted into a ceramic system, during which the structure of the mineral support matrix should be retained as far as possible. The implants obtained from bone in particular have an ideal pore structure, these having a support matrix of bars, cross-pieces and links with pores which interconnect on all sides and pore sizes of up to about 2.5 mm and building up a support matrix appropriate for the loading direction. Because they are an excellent match with the pore system of natural bone, bone ceramic implants therefore have considerable biological advantages in their growing-in properties and healing in the organism.

In addition to these advantages, however, bone ceramic implants also have a number of disadvantages.

Firstly, their production from natural bone material is extremely time- and labor-intensive, especially if the mineralization and sintering to give the ceramic is to be carried out under such mild conditions that practically no changes in structure occur. Corresponding production processes are described, for example, in EP 141 004 and DE-PS 37 27 606.

Secondly, because of the natural origin of the starting materials, the implant materials are limited in construction size, so that not all shapes and dimensions can be realized in the form of one-piece bone ceramics. Since the implants do not correspond to the bone or bone regions to be replaced in their structural build-up and, because of the conversion into a ceramic system, in density, strength and elasticity, a loosening or even breaking off of the implant is to be feared under load as a result of inadequate distribution and transmission of forces.

Another disadvantage of bone ceramic is that the natural product of bone employed as the starting material is subject to considerable inherent and uncontrollable variations in the chemical composition of its mineral phase. Such variations in composition have quite clearly detectable influences on the biological activity of the bone ceramic implant, which manifests itself clinically in different growing-in and bone regeneration rates.

The invention was therefore based on an object of discovering a process for the production of shaped implants for bone replacement with which process such implants can be built up from synthetic starting materials without limitations as to shape and dimensions and at the same time can be structured in a predeterminable manner such that the pore and link system as far as possible corresponds to human bone.

According to such an invention, the object is achieved in that the shaped implant is built up in layers in repeated sequence by production of layers structured in an image-wise manner corresponding to the pore system, and solidification thereof, from a composition which is based on calcium phosphate and can undergo plastic deformation and then be solidified, the image structures of the individual layers being transferred from natural bone, which serves as a model, and the shaped article finally being sintered to give the ceramic.

It has been found that the process is limited neither to the material as such nor to the use for production of shaped implants. From the material point of view, in addition to calcium phosphate ceramics, it is also possible to employ oxide ceramics, glass ceramics, non-ceramic mineral materials, organic polymer materials and, if appropriate, the particular precursors of the materials mentioned, and furthermore also composite materials of two or more of the abovementioned materials, provided that they can be processed in the form of compositions which can undergo plastic deformation and then be solidified. The production of layers structured in an image-wise manner must be possible with such compositions, and subsequent solidification can be carried out by drying, chemical hardening, heat treatment or sintering, depending on the choice of material, the specific composition and the processing requirements. In principle, any desired porous shaped articles having a predetermined pore structure can be produced by the process in all conceivable shapes and dimensions, which ultimately are limited only by the production technology. Such shaped articles can be envisaged for the most diverse intended uses.

The invention thus relates to a process for the production of a porous shaped article by shaping a composition which can undergo plastic deformation and then be solidified, which is characterized in that, to achieve a predetermined pore structure, the shaped article is built up in the form of layers by repeated sequence of the steps production of a layer of the composition structured in an image-wise manner corresponding to the pore system, and solidification of the layer the image structures of the individual layers being transferred from corresponding models.

The invention particularly relates to such a process in which a ceramic composition is employed, the step of solidification of the layer being carried out by drying and the shaped article produced being sintered in a concluding step.

The invention furthermore relates to the use of such a process for the production of shaped articles having a three-dimensional interconnecting pore system, in particular for the production of shaped implants having the pore system of natural bone.

The process according to the invention for the production of porous shaped articles having a predetermined pore structure is based in all its possible embodiments on the process principle that first the image information of the structure of a model, that is to say of a porous body which serves as a sample and the pore structure of which is to be copied, basically, is recorded in layers and is stored in a form suitable for the particular production technique and then used to control the build-up of the shaped article in layers. In the case of actual bodies which serve as the model, the recording and storage of the image information can be effected, for example, by removal of material from the body in layers by cutting, sawing or grinding and photographic recording of the particular layer surfaces. However, the pore system image can also be constructed artificially and be in the form of technical drawings of the layer images or of corresponding image representations.

It is particularly advantageous to carry out the step of recording and storage of the layer image information in a computer-assisted and digitized form. Thus, for example, the photographic layer recordings or the layer images produced in another manner can be transferred to a computer, advantageously to a CAD/CAM system, by means of a laser scanner. It is also possible to record layer structure images by means of computer tomography (CT) and to transfer them to the computer system. The latter process is particularly suitable for transfer of bone structures for the production of shaped implants.

The transfer of the image information for building up the porous shaped article in layers from a suitable preselected material can be carried out in the form of the screen printing technique in the simplest case, the photographic layer recordings or layer images produced in another manner being transferred to screen-printing fabric or screen-printing films in a manner known per se. The material, which must be screen-printable, that is to say it must be able to undergo corresponding plastic deformation and then be solidified, is printed on a substrate through the first screen. After solidification, printing is done through the second screen and so on, until the shaped article has been finished.

This procedure can of course also be realized in a computer-assisted manner, in which case, for example, the layer image information is again available in a CAD/CAM system, and both the screen printing films are produced and a corresponding screen printing unit for building up the shaped article is operated by program control.

Sprayable materials can also be processed by the spray technique, the individual layers being built up by three-dimensionally controllable nozzles or nozzle systems. Precisely with this technique it is particularly advantageous for control of the nozzles to be computer-assisted and program-controlled with the aid of a CAD/CAM system. Combination of digitized image recording, control and processing with program-controlled spray nozzle control enables an elegant, fully automatic procedure for the process according to the invention. Conventional systems and corresponding control programs, which can easily be set up by the relevant expert for the specific requirements of the process according to the invention, can be employed for this purpose.

It goes without saying that this process principle can be applied to virtually all materials which can undergo plastic deformation and then be solidified, that is to say which can be processed in layers. These can preferably be plasticized or liquefied ceramic compositions which are solidified between the layer build-up steps by drying and sintered in a concluding step. Examples of these are calcium phosphate ceramics, oxide ceramics and glass ceramics or their corresponding precursors. The shrinkage typical of ceramic compositions must be taken into account when calculating the dimensions of the layer build-up and of the detailed structures.

Non-ceramic mineral compositions, such as, for example, hydraulic cements and similar materials, furthermore can be processed according to the invention.

Other materials which can be processed according to the invention can be based on high molecular weight, polymeric and/or polymerizable organic compounds. Examples of these are waxes and formulations based on solvent-drying or fusible synthetic resins and reactive resin systems.

Finally, correspondingly processable composite materials of two or more of the abovementioned materials, preferably of ceramic particles and organic polymer materials, can also be employed.

It also goes without saying that the process principle on which the invention is based can also be used for the production of shaped articles of practically any desired dimensions and shape and any desired pore structure. Their later intended use is not subject to any limitation. A preferred field of use is the production of shaped articles having a three-dimensional interconnecting pore system, in particular the production of shaped implants having the pore system of natural bone.

It is also a particular advantage of the process according to the invention that in the case of artificial build-up of porous shaped articles with the aid of corresponding models, selected structural changes can be provided and undertaken if required. Such structural changes can be, for example, in the sense of a selected local reinforcement.

Shaped implants for bone replacement can be provided with additional hollow spaces for accommodation of pharmaceutical active compounds. In this way, for example, antibiotics or growth regulators can be placed in the implant in a pharmaceutically defined local manner, the proportions of which match the requirements of the healing process. Loading of the implant essentially homogeneously over the volume, in accordance with the prior art, with the overdose automatically necessary can thus be avoided.

The procedure for the process according to the invention is illustrated in more detail below by way of example by the production of shaped implants for bone replacement.

Shaped implants can be produced either in the form of a positive or in the form of a negative image of the bone or bone region to be replaced.

The positive form is to be preferred if the implant is to be made of non-absorbable calcium phosphate ceramic, such as, in particular, hydroxyapatite ceramic. The implant then essentially heals in by endogenous tissue sprouting into the pore hollow spaces of the shaped implant, which very largely correspond to natural bone. The production of the shaped implant can be produced [sic] in accordance with the process principle described generally above, for example in accordance with the following process variants:

EMBODIMENT VARIANT 1

Material is removed in layers from natural bone which has been freed from organic contents by known processes. A photographic recording of each layer surface is made. These recordings or the layer surfaces directly are transferred into a CAD/CAM system by means of a laser scanner. Alignment and duplication of the layer recordings are carried out in the computer system. These individual layers are transferred to positive film, with which corresponding print screens are produced.

Synthetically precipitated hydroxyapatite is processed to a liquefied ceramic composition using a customary organic liquefier.

This composition is now printed to a layer on a substrate with the first screen. Drying with hot air follows. The second layer is applied to the first dried ceramic layer with the screen of the second pore layer recording and is again dried. This procedure is followed until all the layers have been printed and a ceramic green compact is obtained. The resulting green compact can additionally be rinsed with a ceramic slip of the same composition to smooth the layer transitions.

The green compact is then sintered to a ceramic, for example with a sinter program which provides a heating-up rate of 50 K/minute up to a temperature of about 1300°C. and then a holding time of 2 hours. After cooling, the ceramic shaped article is finished.

If required, mechanical final shaping can then also follow, which gives any desired implant shape by customary methods (grinding, turning, milling, drilling etc.)

EMBODIMENT VARIANT 2

The layer images stored in the computer system according to Variant 1 are applied in layers, with intermediate drying phases, by means of a CAD/CAM-controlled spray or discharge nozzle charged with the ceramic slip. The green compact thus obtained is further processed to a ceramic analogously to Variant 1.

A shaped implant in the form of a negative image of the bone structure is suitable if a bioabsorbable material is to be employed. Such a shaped implant essentially heals in by the material slowly being worn away by bioabsorption mechanisms and at the same time being replaced by endogenous tissue growing in, in particular by regenerated mineralized bone matrix.

Such a shaped implant can be produced in accordance with the process principle described generally, for example in accordance with the following process variants:

EMBODIMENT VARIANT 3

A temporary positive shaped article is first produced by the screen-printing or spray process in accordance with the layer images stored in the computer system. A readily fusible or soluble composition, for example wax, is advantageously used as the material here. This body is then impregnated with a highly liquefied ceramic slip based on bioabsorbable tricalcium phosphate and dried. The body is now heated above the melting point of the wax, so that the wax runs out of the body. The resulting ceramic green compact with the negative of the pore and link system of a natural bone is now further processed to a ceramic analogously to Variant 1. A bioabsorbable shaped implant based on tricalcium phosphate ceramic is obtained.

EMBODIMENT VARIANT 4

A shaped article which corresponds to the negative of the pore and link system of natural bone is built up by the screen-printing or spray process in accordance with the layer images stored in the computer system using a ceramic slip based on tricalcium phosphate. Further processing of the ceramic green compact to the ceramic shaped implant is carried out in a known manner.

In addition to ceramic compositions based on bioabsorbable calcium phosphates, it is also possible for other bioabsorbable materials to be processed in this variant. Examples of these are bioabsorbable polymers, for example polylactides and polyglycolides, and partly or completely absorbable composite materials based on calcium phosphate particles and the abovementioned polymers.

Shaped articles for any desired other intended uses can also be produced by the process according to the invention for the production of porous shaped articles having a predetermined pore structure.

An example of these are ceramic catalyst supports for exhaust purification in motor vehicles. According to the current technique, extruded honeycombed shaped articles which have only longitudinal pores, in accordance with this production method, are used for this. Ceramic catalyst supports which have a three-dimensional interconnecting pore structure and are produced by the process according to the invention can be increased in their effectiveness and reduced in structural size because of a considerably higher internal surface area.

Other fields of use are porous bodies for filter technology or as static mixers for gases or liquids. The flow properties here can be optimized by controlled build-up of the porosity.

Another example are porous ceramic shaped articles which are used as sorbents for chromatography columns. Here also, flow properties and effectiveness can be optimized by a preselected pore structure. Chromatography columns with packings in the form of ready-made, solid, porous, ceramic shaped sorbents render expensive column packing procedures superfluous and also are not subject to a change in density. A ceramic sorbent can also be regenerated without problems, for example by thorough baking at a correspondingly high temperature, depending on the base material.

We claim:

1. A process for the production of a porous shaped article from a composition which can undergo plastic deformation and solidification, said article having a predetermined three-dimensional interconnecting pore structure with the configuration of natural spongiosa bone, said process comprising building up the shaped article in the form of layers by repeated sequence of production of a layer of the composition according to a predetermined image of solid portions and a pore system corresponding to a portion of the pore structure of natural spongiosa bone, whereby the composition is deposited where the article is to be solid and is not deposited where the pore system is to be, and solidification of the layer.

2. A process according to claim 1, wherein the layers of the composition are applied by spraying.

3. A process according to claim 1, wherein the build-up of the layers according to the image is program controlled.

4. A process according to claim 3, wherein the image is in digitized form.

5. A process according to claim 1, wherein a ceramic composition is employed, the solidification of the layer being carried out by drying and the shaped article produced after all layers are completed being sintered.

6. A process according to claim 1, wherein a composition based on polymerizable organic compounds and/or organic polymer materials is employed.

7. A process according to claim 1, wherein a composition based on a composite material of ceramic particles and organic polymer materials is employed.

8. A process according to claim 1, wherein the layers of the composition are applied by means of screen printing.

* * * * *